(12) United States Patent
Roymans et al.

(10) Patent No.: US 8,137,921 B2
(45) Date of Patent: Mar. 20, 2012

(54) HOMOGENEOUS TIME RESOLVED FLUORESCENCE BASED TEST SYSTEM FOR PARAMYXOVIRIDAE

(75) Inventors: Dirk André E Roymans, Turnhout (BE); Koenraad Lodewijk August van Acker, Temse (BE); Inge Vereycken, Deurne (BE); Géry Karel Julia Dams, Paal-Beringen (BE)

(73) Assignee: Tibotec BVBA, Mechelen (BE)

( * ) Notice: Subject to any disclaimer, the term of this patent is extended or adjusted under 35 U.S.C. 154(b) by 170 days.

(21) Appl. No.: 12/513,594

(22) PCT Filed: Dec. 12, 2007

(86) PCT No.: PCT/EP2007/063753
§ 371 (c)(1),
(2), (4) Date: May 5, 2009

(87) PCT Pub. No.: WO2008/071723
PCT Pub. Date: Jun. 19, 2008

(65) Prior Publication Data
US 2010/0035363 A1    Feb. 11, 2010

(30) Foreign Application Priority Data
Dec. 12, 2006   (EP) .................................... 06125876

(51) Int. Cl.
*G01N 33/53* (2006.01)
*A61K 39/155* (2006.01)

(52) U.S. Cl. ....................................... 435/7.1; 424/211.1
(58) Field of Classification Search .................. None
See application file for complete search history.

(56) References Cited

U.S. PATENT DOCUMENTS
2002/0077284 A1   6/2002   Eckert et al.

FOREIGN PATENT DOCUMENTS
WO   WO 01/40274   6/2001

OTHER PUBLICATIONS

John Comley, Drug Discovery World, Spring, 2006, pp. 22-37.*
Eckert et al., J. Mol. Biol., 1998, 284:859-865.*
Invitrogen, Alexa Fluor Dyes Spanning the Visible and Infrared Spectrum, Section 1.3, first three pages, printed from this website on Oct. 19, 2011: http://www.invitrogen.com/site/us/en/home/References/Molecular-Probes-The-Handbook/Fluorophores-and-Their-Amine-Reactive-Derivatives/Alexa-Fluor-Dyes-Spanning-the-Visible-and-Infrared-Spectrum.html.*
Gochin, Miriam et al. "A Fluorescence Assay for Rapid Detection of Ligand Binding Affinity to HIV-1 gp41". Biological Chemistry, vol. 387, No. 4, Apr. 2006, pp. 477-483, XP002431422.
Zhao, X. et al. "Structural Characterization of the HumanRespiratory Syncytial Virus Fusion Protein Core". Proceedings of the National Academy of Sciences of the United States of America, vol. 97, No. 26, Dec. 19, 2000, XP002431420.
Selvin, P.R. "Principles and Biophysical Applications of Lanthanide-Based Probes". Annual Review of Biophysics and Biomolecular Structure, Annual Reviews Inc., Palo Alto, CA., vol. 31, 2002, pp. 275-302, XP008060956.
Wang, E. et al. "both Heptad Repeats of Human Respiratory Syncytial Virus Fusion Protein are Potent Inhibitors of Viral Fusion". Biochemical and Biophysical Research Communications, vol. 302, No. 3, Mar. 14, 2003, pp. 469-475, XP002431421.
Sreerama, N. et al., A Self-Consistent Method for the Analysis of Protein Secondary Structure fro Circular Dichroism, *Analytical Biochemistry*, 1993; 209:32-44.

* cited by examiner

*Primary Examiner* — Stacy B. Chen
(74) *Attorney, Agent, or Firm* — Woodcock Washburn LLP

(57) ABSTRACT

The present invention concerns a fluorescence resonance energy transfer based high throughput test system to measure the formation of the RSV F1 six-helix bundle. In a first embodiment the current invention relates to a homogeneous time resolved fluorescence-based test system comprising a first helical polypeptide consisting essentially of the sequence of IQN57 (SEQ ID NO: 1); a second helical polypeptide consisting essentially of the sequence of C45 (SEQ ID NO: 2) wherein said IQN57 is labeled with a light emitting fluorophore and said C45 is labeled with an ultra-violet excitable fluorophore.

17 Claims, No Drawings

SEQUENCE LISTING

<160> NUMBER OF SEQ ID NOS: 4

<210> SEQ ID NO 1
<211> LENGTH: 85
<212> TYPE: PRT
<213> ORGANISM: respiratory syncytial virus

<400> SEQUENCE: 1

```
Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Ala Val Ser Lys
            20                  25                  30

Val Leu His Leu Glu Gly Glu Val Asn Lys Ile Lys Ser Ala Leu Leu
        35                  40                  45

Ser Thr Asn Lys Ala Val Val Ser Leu Ser Asn Gly Val Ser Val Leu
    50                  55                  60

Thr Ser Lys Val Leu Asp Leu Lys Asn Tyr Ile Asp Lys Gln Leu Leu
65                  70                  75                  80

Pro Ile Val Asn Lys
                85
```

<210> SEQ ID NO 2
<211> LENGTH: 45
<212> TYPE: PRT
<213> ORGANISM: respiratory syncytial virus

<400> SEQUENCE: 2

```
Asn Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu Ala Phe Ile Arg
            20                  25                  30

Lys Ser Asp Glu Leu Leu His Asn Val Asn Ala Gly Lys
        35                  40                  45
```

```
<210> SEQ ID NO 3
<211> LENGTH: 83
<212> TYPE: PRT
<213> ORGANISM: respiratory syncytial virus

<400> SEQUENCE: 3

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Ile Gly Glu
            20                  25                  30

Val Leu His Leu Glu Gly Glu Val Asn Lys Ile Lys Ser Ala Leu Leu
        35                  40                  45

Ser Thr Asn Lys Ala Val Val Ser Leu Ser Asn Gly Val Ser Val Leu
    50                  55                  60

Thr Ser Lys Val Leu Asp Leu Lys Asn Tyr Ile Asp Lys Gln Leu Leu
65                  70                  75                  80

Pro Ile Val

<210> SEQ ID NO 4
<211> LENGTH: 39
<212> TYPE: PRT
<213> ORGANISM: respiratory syncytial virus

<400> SEQUENCE: 4

Val Phe Pro Ser Asp Glu Phe Asp Ala Ser Ile Ser Gln Val Asn Glu
1               5                   10                  15

Lys Ile Asn Gln Ser Leu Ala Phe Ile Arg Lys Ser Asp Glu Leu Leu
            20                  25                  30

His Asn Val Asn Ala Gly Lys
            35
```

HOMOGENEOUS TIME RESOLVED FLUORESCENCE BASED TEST SYSTEM FOR PARAMYXOVIRIDAE

CROSS REFERENCE TO RELATED APPLICATIONS

This application is the national stage of PCT Application No. PCT/EP2007/063753 filed Dec. 12, 2007, which claims priority from European Patent Application No. 06125876.0, filed Dec. 12, 2006, the entire disclosures of which are hereby incorporated in their entirety.

Human RSV or Respiratory Syncytial Virus is a negative strand RNA virus, member of the family of Paramyxoviridae, subfamily pneumovirinae. RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In elderly, susceptibility again increases, and RSV has been implicated in a number of outbreaks of pneumonia resulting in significant mortality.

There are two major antigenic groups of RSV, A and B, and additional antigenic variability occurs within the groups. Infection with a virus from a given subgroup does not protect against a subsequent infection with an RSV isolate from the same subgroup in the following winter season. Re-infection with RSV is thus common, despite the existence of only two subtypes.

Today only three drugs have been approved for use against RSV infection. Ribavirin, a nucleoside analogue, provides an aerosol treatment for serious RSV infection in hospitalized children. The highly variable efficacy, the toxicity (risk of teratogenicity), the aerosol route of administration and the cost, limit its use. The other two drugs, RESPIGAM® and SYNAGIS® (palivizumab), polyclonal and monoclonal antibody immunostimulants, are intended to be used in a preventive way. Attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

RSV is surrounded by a lipid bi-layer bearing three surface glycoproteins: F, G and SH. The most extensive antigenic and genetic diversity is found in the G-protein, whereas the F protein (fusion protein) is highly conserved across subtypes. Hence, it is believed that F-inhibitors will be active in all RSV subtypes. The F protein is crucial for viral entry into its host cell and thus plays a critical role in infection. Prophylactic therapy is currently pursued with RSV-specific monoclonal antibodies that target the F protein of the virus.

The F protein is synthesized as a 67 kDa precursor (F0) that is processed by proteolytic cleavage to yield two disulfide-linked subunits: F1 and F2. The molecular sequence of F1 includes the so-called "heptad-repeat" regions HR1 and HR2 sometimes also referred as HRA and HRB respectively. Synonyms for HR1 and HR2 include HR-N and HR-C respectively. A heptad-repeat is a type of tandem repeat sequence in which a group of seven amino acids occurs many times in a protein sequence.

The F protein mediates fusion of the membranes of the virus and target cell, allowing RSV to infect new cells and eventually to replicate. The process of membrane fusion involves a conformational change in the F protein, exposing in the target cell membrane a trimeric coiled coil formed by alpha helices from the N-terminal region of each of the three F1 subunits (HR1). This coiled coil interacts with alpha helices from the C-terminal region of the three F1 subunits (HR2). The resulting hexameric alpha helical interaction between the HR1 and HR2 regions of F1 fuses the viral and cellular membranes.

Proteolytic studies were used to identify the F1 segments responsible for formation of the hexameric fusion intermediate, called N57 and C45 (X. Zhao et al., Proc Natl Acad Sci USA 97:14172-14177 (2000); incorporated herein by reference). They contain the "heptad-repeat" regions HR1 and HR2, respectively. Intriguingly, residues within the N57 and C45 regions are some of the most highly conserved residues of the F protein coding region of the RSV genome. Synthetic peptides corresponding to these regions have been shown to inhibit RSV infectivity in vitro, suggesting that they act as inhibitors of F1-protein mediated membrane fusion. These results indicated that an isolated complex between peptides comprising amino acid sequences from the N57 and C45 regions would be a good model of the F1 fusogenic intermediate.

Synthetic N57 and C45 peptides were shown to form a stable hexameric structure under appropriate conditions in vitro, indicating that peptides containing amino acid sequences from these regions can form the hexameric F1 core in the absence of the remainder of the F1 protein. The X-ray crystal structure of the N57/C45 complex was determined by X. Zhao et al. The structure revealed the three C45 peptides representing the HR2 regions of F1 were packing in an antiparallel fashion against the three N57 peptides representing HR1 regions, forming a six-helix bundle. Trimming the N57/C45 complex by proteinase K generated the core complex N51/C39 that had the same stability as N57/C45. Twenty amino acid residues from each C45 peptide and 26 residues from two adjacent N57 peptides contribute to the interface interaction. These residues are highly conserved among different RSV strains. Most of the amino acid differences between strains are limited to conservative mutations.

HR1 and HR2 regions form trimeric hairpin-like structures, with the three HR2's packing in an antiparallel manner against the three hydrophobic grooves of the inner coiled coil formed by the three HR1's. Within the cavity region, the majority of contacts are between six cavity-lining residues from the N57 peptides (Lys 191, Leu 195, and Tyr 198 from one chain and Lys 196, Asp 200, and Leu 204 from another) and two aromatic residues, Phe 483 and Phe 488, from the C45 peptide.

The part of the F protein that enters the host cell membrane is situated at the N terminus of the F1 peptide, while the transmembrane segment that is anchored in the viral membrane, is located close to the C terminus. Adjacent to these two regions are the two heptad repeat sequences (HR1 and HR2), that form stable trimers of hairpins-like structure that undergo a conformational change to enable the viral and cell membranes to be apposed prior to viral entry.

This hydrophobic interaction is an attractive target for candidate fusion inhibitors. While this interaction is present in the N57/C45 peptide complex, this complex is not ideally suited for screening of potential F1 inhibitors because N57 is insoluble and subject to aggregation in the absence of C45. Therefore, a soluble fusion peptide comprising N57 and 29 residues of the soluble trimeric coiled-coil GCN4-pI$_Q$I was constructed. This peptide, called IQN57, has the sequence RMKQIEDKIEEIESKQKKIENE-IARIKKAVSKVLHLEGEVNKIKSALLSTNKAVVS LSNGVSVLTSKVLDLKNYIDKQLLPIVNK (SEQ ID NO: 1), with the RSV F1 sequence of amino acids underlined. IQN57 includes 3 mutations of surface residues in the GCN4-pI$_Q$I region to improve solubility. It is fully helical, with nearly the same superhelix parameters as the F1 N-helix, and forms a stable trimer in solution.

On another aspect, goals of drug design initially comprise the characterization of selectivity and affinity, efficacy, toxicity (therapeutic window/safety margin), pharmacokinetics, and stability, for a given compound like above mentioned candidate fusion inhibitors. One of the earlier steps in drug design and discovery is focused on discriminating potential active compounds amongst a large variety of chemical compounds. This discrimination of potential active chemical structures is suitably accomplished by ligand-binding assays. Ligand-binding assays measure the affinity and/or degree of a drug to remain associated with a receptor. Within a molecule structure, the affinity or degree of binding of a specific moiety for a target recognition site of the receptor is particularly useful information in designing and optimizing effective compounds against a given target. Additionally, ligand-binding assays are especially convenient in elucidating mechanisms of action or inhibition.

Although screening assays for fusion inhibitors have been available for some time, mechanistic studies of RSV fusion inhibitors targeted to F1 have been hampered by the lack of sensitive methodologies, which may discriminate between a large range of degrees of binding, leaving a tremendous range of chemical diversity untested.

One of the known screening assays is the so-called capillary zone electrophoresis (CZE) allowing the detection and discrimination of compounds or moieties of compounds useful for designing RSV fusion inhibitors. With CZE the degree of complex formation between two helical peptides can be identified. The endpoint of this technology relies on disruption of the complexing peptides. However, compounds inducing subtle distortions of peptide interactions exhibit equal anti-fusion activity.

A model and the means for directly measuring ligand-binding with high sensitivity and robustness is highly desired for screening a broader window of anti-fusion compounds.

In accordance with the present invention, it has now been found that a fluorescence resonance energy transfer based test system detects distortion as well as disruption of the peptide interaction by any tested compound, because angstrom scale distance changes lead to signal changes. In addition, the throughput, by using the test system according to the invention, for compound evaluation is much higher compared to e.g. the CZE technology.

The test system according to the invention also circumvents the classical problem encountered in fluorescence assays of intrinsic fluorescent properties of many test compounds by using europium. Europium exhibits an exceptionally long-lived fluorescence and thus the energy transfer to allophycocyanin is measured milliseconds after excitation when intrinsic compound fluorescence is less significant.

The present invention relates to a fluorescence resonance energy transfer based high throughput test system to measure the formation of the six-helix bundle.

Many compounds and proteins present in biological fluids or serum are naturally fluorescent, and the use of conventional fluorophores may lead to serious limitations of sensitivity. Most of these background signals being short-lived, the use of long-lived labels combined with detection on a time-resolved fluorescence basis surprisingly allow the minimization of prompt interferences.

In the fluorescence resonance energy transfer technology the dependence of the energy transfer rate is postulated on the inverse sixth power of the distance between an excited fluorescent donor and a nearby acceptor molecule.

In a first embodiment the current invention relates to a homogeneous time resolved fluorescence-based test system for paramyxoviridae comprising a first helical polypeptide consisting essentially of a sequence derived from the N-helix heptad-repeat region (HR1) of RSV and a second helical polypeptide consisting essentially of a sequence derived from the C-helix heptad-repeat (HR2) region of RSV.

The first helical polypeptide is labeled with a light emitting fluorophore while the second helical polypeptide is labeled with a ultra-violet excitable fluorophore. Alternatively, the first helical polypeptide is labeled with a ultra-violet excitable fluorophore while the second helical polypeptide is labeled with a light emitting fluorophore.

In a preferred embodiment the first helical polypeptide consists essentially of the sequence of IQN57 (SEQ ID NO: 1) while the second helical polypeptide consists essentially of the sequence of C45 (SEQ ID NO: 2) wherein said IQN57 is labeled with a light emitting fluorophore and said C45 is labeled with an ultra-violet excitable fluorophore.

Alternatively, the IQN57 sequence is labeled with a ultra-violet excitable fluorophore while the C45 sequence is labeled with a light emitting fluorophore.

The IQN57 sequence may comprise a linker between the label and the IQ-moiety of the IQN57 sequence. Preferably, the linker is attached to the N-terminal IQ-end of the IQN57 sequence.

The linker is selected from the group of an antibody-antibody complex, antibody-antigen complex or streptavidin-biotin system.

The ultra-violet excitable fluorophore is selected from the group of lanthanides and wherein the light emitting fluorophore matches the excitation wavelength of the selected lanthanide.

Preferably, the light emitting fluorophore is allophycocyanin, more preferably streptavidin-allophycocyanin, and the ultra-violet excitable fluorophore is europium.

Other light emitting fluorophores are selected from the group of ALEXA FLUOR® 546 sulfonated rhodamine having an optimal excitation wavelength at 546 nm, rhodamine or Cy3 and wherein the ultra-violetexcitable fluorophore is terbium.

Part of the invention is also a method for identifying a compound that interferes with the formation of the RSV six-helix bundle of F1 comprising:

providing a first helical polypeptide consisting essentially of the sequence derived from the heptad-repeat 1 (HR1) region of RSV, preferably wherein said polypeptide consists essentially of the sequence of IQN57 (SEQ ID NO:1);

providing a second helical polypeptide consisting essentially of the sequence derived from the heptad-repeat 2 (HR2) region of RSV, preferably wherein said polypeptide consists essentially of the sequence of C45 (SEQ ID NO: 2);

wherein said IQN57 is labeled with a light emitting fluorophore and said C45 is labeled with an ultra-violet excitable fluorophore;

providing a test composition comprising the compound;

measuring the degree of complex formation between the first helical poly-peptide and the second helical polypeptide in the presence of the test composition comprising the compound using fluorescence resonance energy transfer; and comparing the measured degree of complex formation to the degree of complex formation between the first helical polypeptide and the second helical polypeptide in the absence of the test composition comprising the compound to identify the compound that interferes with the formation of the RSV six-helix bundle of F1.

Said IQN57 sequence may comprise a linker between the label and the IQ-moiety of the IQN57 sequence, preferably the linker is attached to the N-terminal IQ-end of the IQN57 sequence.

The linker is selected from the group of an antibody-antibody complex, antibody-antigen complex or streptavidin-biotin system.

The ultra-violet excitable fluorophore is selected from the group of lanthanides and wherein the light emitting fluorophore matches the excitation wavelength of the selected lanthanide.

Preferably, the light emitting fluorophore is allophycocyanin, more preferably streptavidin-allophycocyanin, and the ultra-violet excitable fluorophore is europium.

Other light emitting fluorophores for use in the method are selected from the group of ALEXA FLUOR® 546 sulfonated rhodamine having an optimal excitation wavelength at 546 nm, rhodamine or Cy3 and wherein the ultra-violet excitable fluorophore is terbium.

Another embodiment of the present invention is a method for identifying the mechanism of inhibition of the formation of the RSV six-helix bundle of F1 comprising:

providing a first helical polypeptide consisting essentially of the sequence of IQN57 (SEQ ID NO:1);

providing a second helical polypeptide consisting essentially of the sequence of C45 (SEQ ID NO: 2) wherein said IQN57 is labeled with a light emitting fluorophore and said C45 is labeled with an ultra-violet excitable fluorophore;

providing a test composition comprising a compound that interferes with the formation of the six-helix bundle of F1;

measuring the degree of complex formation between the first helical polypeptide and the second helical polypeptide in the presence of the test composition comprising a compound that interferes with the formation of the six-helix bundle of F1 using fluorescence resonance energy transfer; and comparing the measured degree of complex formation to the degree of complex formation between the first helical polypeptide and the second helical polypeptide in the absence of the test composition comprising the compound that interferes with the formation of the six-helix bundle of F1 to identify the mechanism of inhibition of the formation of the RSV six-helix bundle of F1.

In another embodiment the first helical polypeptide consists essentially of the sequence of IQN51 (SEQ ID NO: 3) while the second helical polypeptide consists essentially of the sequence of C39 (SEQ ID NO: 4) wherein said IQN51 is labeled with a light emitting fluorophore and said C39 is labeled with an ultra-violet excitable fluorophore.

Alternatively, the IQN51 sequence is labeled with a ultra-violet excitable fluorophore while the C39 sequence is labeled with a light emitting fluorophore.

The IQN51 sequence may comprise a linker between the label and the IQ-moiety of the IQN51 sequence. Preferably, the linker is attached to the N-terminal IQ-end of the IQN51 sequence.

The linker is selected from the group of an antibody-antibody complex, antibody-antigen complex or streptavidin-biotin system.

The ultra-violet excitable fluorophore is selected from the group of lanthanides and wherein the light emitting fluorophore matches the excitation wavelength of the selected lanthanide.

Preferably, the light emitting fluorophore is allophycocyanin, more preferably streptavidin-allophycocyanin, and the ultra-violet excitable fluorophore is europium.

Other light emitting fluorophores are selected from the group of ALEXA FLUOR® 546 sulfonated rhodamine having an optimal excitation wavelength at 546 nm, rhodamine or Cy3 and wherein the ultra-violet excitable fluorophore is terbium.

Part of the invention is also the method for identifying a compound that interferes with the formation of the RSV six-helix bundle of F1 comprising:

providing a first helical polypeptide consisting essentially of the sequence derived from the heptad-repeat 1 (HR1) region of RSV, preferably wherein said polypeptide consists essentially of the sequence of IQN51 (SEQ ID NO:3);

providing a second helical polypeptide consisting essentially of the sequence derived from the heptad-repeat 2 (HR2) region of RSV, preferably wherein said polypeptide consists essentially of the sequence of C39 (SEQ ID NO: 4);

wherein said IQN51 is labeled with a light emitting fluorophore and said C39 is labeled with an ultra-violet excitable fluorophore;

providing a test composition comprising the compound;

measuring the degree of complex formation between the first helical polypeptide and the second helical polypeptide in the presence of the test composition comprising the compound using fluorescence resonance energy transfer; and comparing the measured degree of complex formation to the degree of complex formation between the first helical polypeptide and the second helical polypeptide in the absence of the test composition comprising the compound to identify the compound that interferes with the formation of the RSV six-helix bundle of F1.

Said IQN51 sequence may comprise a linker between the label and the IQ-moiety of the IQN51 sequence, preferably the linker is attached to the N-terminal IQ-end of the IQN51 sequence.

The linker is selected from the group of an antibody-antibody complex, antibody-antigen complex or streptavidin-biotin system.

The ultra-violet excitable fluorophore is selected from the group of lanthanides and wherein the light emitting fluorophore matches the excitation wavelength of the selected lanthanide.

Preferably, the light emitting fluorophore is allophycocyanin, more preferably streptavidin-allophycocyanin, and the ultra-violet excitable fluorophore is europium.

Other light emitting fluorophores for use in the method are selected from the group of ALEXA FLUOR® 546 sulfonated rhodamine having an optimal excitation wavelength at 546 nm, rhodamine or Cy3 and wherein the ultra-violet excitable fluorophore is terbium.

Another embodiment of the present invention is the method for identifying the mechanism of inhibition of the formation of the RSV six-helix bundle of F1 comprising:

providing a first helical polypeptide consisting essentially of the sequence of IQN51 (SEQ ID NO:3);

providing a second helical polypeptide consisting essentially of the sequence of C39 (SEQ ID NO: 4) wherein said IQN51 is labeled with a light emitting fluorophore and said C39 is labeled with an ultra-violet excitable fluorophore;

providing a test composition comprising a compound that interferes with the formation of the six-helix bundle of F1;

measuring the degree of complex formation between the first helical polypeptide and the second helical polypeptide in the presence of the test composition comprising a compound that interferes with the formation of the six-helix bundle of F1 using fluorescence resonance energy transfer; and comparing the measured degree of complex formation to the degree of complex formation between the first helical polypeptide and the second helical polypeptide in the absence of the test composition comprising the compound that interferes with the formation of the six-helix bundle of F1 to identify the mechanism of inhibition of the formation of the RSV six-helix bundle of F1.

The above described combinations IQN57/C45 and IQN51/C39 can be adapted within the scope of the invention to IQN57/C39 and IQN51/C45 respectively.

The peptides or compounds identified by the above-mentioned method are listed in the Example section of the present description and the thus identified peptides or compounds can be used for inhibiting the formation of the RSV six-helix bundle of F1.

These terms as used herein are defined as follows:

Helical polypeptide as used herein refers to a polypeptide with a helical content of at least 70% in aqueous solution, such as for example 74%, 80%, 85%, 90% and 95%. The percent helical content is estimated as previously described (Sreerama et al., Anal. Biochem. 209:32-44 (1993)).

A fusion inhibitor, as used herein, is any compound that prevents membrane fusion between target cells and free virus or viral infected cells. For example, an RSV fusion inhibitor may be any compound that binds to F1 and prevents the fusogenic six-helical bundle formation, thus decreases F1-mediated membrane fusion. In one embodiment, a fusion inhibitor is any compound that decreases the degree of complex formation or binding affinity. In another embodiment, a fusion inhibitor is chosen from peptides, derivatized peptides, C-peptides, D-peptides, N-peptides, cyclic or linear, small and large molecules that decrease F1-mediated membrane fusion, including, for example, disrupting the complex formation of the N- and C-helices of F1.

C-peptides are peptide segments derived from the second heptad repeat region of RSV F1 sequence and their derivatives, such as C45 and C39.

N-peptides are peptide segments derived from the first heptad repeat region of RSV F1 sequence and their derivatives such as N57 and N51.

A test composition comprises any compound, including, but not limited to, peptides, dipeptides, tripeptides, polypeptides, proteins, small and large organic molecules and derivatives thereof. Large organic molecules are those with a molecular weight higher than 1000 Daltons.

Complex formation or binding affinity, as used herein, refers to the ability of at least two entities, for example, at least two peptides, to interact with one another, such as, for example, by hydrogen bonding and Van der Waals interactions. The degree of complex formation of two peptides would therefore be the extent of interaction between two peptides. This parameter ranges between 0-100%, with 100% being one peptide completely bound to the other peptide at the experimental concentrations.

The binding affinity of the first helical polypeptide and the second helical polypeptide, both alone and in the presence of the test composition, may be measured by any method known in the art. For example, the binding affinity may be measured by titrating the second helical polypeptide against a fixed concentration of the first helical polypeptide or vice versa.

The degree of complex formation measures the percentage of bound second helical polypeptide relative to the total amount of second helical polypeptide, at fixed concentrations of the first and second helical polypeptides. Although one can calculate binding affinity from the degree of complex formation, this is usually not recommended because of possible large errors. The difference between degree of complex formation and binding affinity is that binding affinity is usually determined by a series of measurements of degree of complex formation at a fixed concentration of one binding component, and at increasing concentrations of the second binding component until the first binding component is completely bound. A titration curve is thus obtained.

By the use of the phrase "consisting essentially of" in describing the sequences of the invention, it is meant to include any changes, variations, derivatives, additions, insertions, and mutations to the sequence of IQN57 and IQN51 and/or C45 and C39 that do not prohibit binding of the first helical polypeptide and the second helical polypeptide.

Peptides mentioned or used in the current description are:

```
(RSV-IQN57)
                                         SEQ ID NO 1
RMKQIEDKIEEIESKQKKIENEIARIKKAVSKVLHLEGEVNKIKSALLST
NKAVVSLSNGVSVLTSKVLDLKNYIDKQLLPIVNK (RSV-C45):
                                         SEQ ID NO 2
NFYDPLVFPSDEFDASISQVNEKINQSLAFIRKSDELLHNVNAGK (RSV-IQN51):
                                         SEQ ID NO 3
RMKQIEDKIEEIESKQKKIENEIARIKKLIGEVLHLEGEVNKIKSALLST
NKAVVSLSNGVSVLTSKVLDLKNYIDKQLLPIV (RSV-C39):
                                         SEQ ID NO 4
VFPSDEFDASISQVNEKINQSLAFIRKSDELLHNVNAGK
```

EXAMPLES

Streptavidin-allophycocyanin (strepatavidin-APC) was purchased from Perkin Elmer. The peptides HIV-C34, HIV-T20, RSV-C45, RSV-C39, biotin-labeled RSV-IQN57 (IQN57-biotin), biotin-labeled RSV-IQN51 (IQN51-biotin), europium-labeled RSV-C45 (C45-Eu) and europium-labeled RSV-C39 (C39-Eu) were all synthesized according to standard protocols.

Test compounds were serially diluted in PBS and then added to 384-well plates. Solutions of strepatavidin-APC (40 nM), IQN57-biotin (400 nM), IQN51-biotin (400 nM), C45-Eu (500 nM) and C39-Eu (500 nM), HIV-C34, HIV-T20, and RSV-C45 and RSV-C39 were prepared in 100 mM Hepes buffer pH 7.2.

Equal volumes of the IQN57-biotin and strepatavidin-APC solution were mixed and incubated for 30 min at room temperature in tubes. Next, these mixes were transferred from the tubes to plates containing test compounds (ratio 2:1) and incubated for 2 h at room temperature. Finally, C45-Eu was added to the wells resulting in final plate concentrations of 10 nM strepatavidin-APC, 100 nM IQN57-biotin, and 25 nM C45-Eu. After incubating the plates for 30 min at room temperature, the fluorescence resonance energy transfer (FRET) signal was detected using a Viewlux reader and used to calculate the 50% inhibitory concentration ($IC_{50}$) of the test compound. $IC_{50}$ is the drug concentration at which 50% of the FRET signal (or 6HB complex formation) is inhibited. A final DMSO percentage of 0.5% was applied. This assay is named the IQN57-APC/C45-Eu assay.

Alternative Assay Set-Up.

In an alternative set-up, equal volumes of the IQN51-biotin and strepatavidin-APC solution were mixed and incubated for 30 min at room temperature in tubes. Next, these mixes were transferred from the tubes to plates containing test compounds (ratio 2:1) and incubated for 2 h at room temperature. Finally, C39-Eu was added to the wells resulting in final plate concentrations of 10 nM strepatavidin-APC, 100 nM IQN51-biotin, and 25 nM C39-Eu. After incubating the plates for 30 min at room temperature, the fluorescence resonance energy transfer (FRET) signal was detected using a Viewlux reader and used to calculate the $IC_{50}$ of the test compound. A final DMSO percentage of 0.5% was applied. This assay is named the IQN51-APC/C39-Eu assay.

The assay principle can be applied to a number of different labels and capture techniques.

Instead of the streptavidin-biotin system for peptide capture to the assay plate, antibodies targeting the peptides can be used.

The europium label can be substituted with other lanthanides such as a terbium label, which exhibit similar properties.

The APC label can be substituted for a number of different labels where the peak of the lanthanide emission matches the excitation wavelength of the label. The preferred matching pair is europium-APC. However, combinations such as (not limited to) terbium ALEXA FLUOR® 546 sulfonated rhodamine having an optimal excitation wavelength at 546 nm, terbium-rhodamine, terbium-FITC and terbium-Cy3 are possible.

Results

A set of established HIV and RSV fusion inhibitors was used to validate the IQN57-APC/C45-Eu and IQN51-APC/C39-Eu assay respectively. Two peptides with reported inhibitory activity against HIV 6-helix bundle formation (T20 and C34, both HIV-derived peptides) showed no inhibitory activity up to 10 μM in both assays. The RSV fusion inhibitors C39 and C45 were active. C39 with $IC_{50}$'s of 0.064 and 0.076 μM respectively, in the IQN57-APC/C45-Eu and IQN51-APC/C39-Eu set-ups. C45 showed $IC_{50}$ values of 0.074 and 0.076 in the respective set-ups.

| $IC_{50}$ (μM) | IQN51-APC/C39-EU | IQN57-APC/C45-EU |
|---|---|---|
| T20 | >10 | >10 |
| C34 | >10 | >10 |
| C39 | 0.076 | 0.064 |
| C45 | 0.076 | 0.074 |

The invention claimed is:

1. A homogeneous time resolved fluorescence-based test system comprising a first helical labeled polypeptide consisting of a sequence from the heptad-repeat 1 (HR1) region of Respiratory Syncytial Virus (RSV); and a second helical labeled polypeptide consisting of a sequence from the heptad-repeat 2 (HR2) region of RSV, wherein the first helical polypeptide consists of the sequence of IQN57 (SEQ ID NO: 1), and the second helical polypeptide consists of the sequence of C45 (SEQ ID NO: 2).

2. A homogeneous time resolved fluorescence-based test system according to claim 1 wherein said IQN57 is labeled with a light emitting fluorophore and said C45 is labeled with an ultra-violet excitable fluorophore.

3. A homogeneous time resolved fluorescence-based test system according to claim 1 wherein said C45 is labeled with a light emitting fluorophore and said IQN57 is labeled with an ultra-violet excitable fluorophore.

4. A homogeneous time resolved fluorescence-based test system according to claim 2 wherein said IQN57 sequence comprises a linker between the label and the IQ-moiety of the IQN57 sequence.

5. A homogeneous time resolved fluorescence-based test system according to claim 4 wherein the linker is attached to the N-terminal IQ-end of the IQN57 sequence.

6. A homogeneous time resolved fluorescence-based test system according to claim 4 or 5 wherein said linker is selected from the group of an antibody-antibody complex, antibody-antigen complex or streptavidin-biotin system.

7. A homogeneous time resolved fluorescence-based test system according to claim 2 wherein the ultra-violet excitable fluorophore is selected from the group of lanthanides and wherein the light emitting fluorophore matches the excitation wavelength of the selected lanthanide.

8. A homogeneous time resolved fluorescence-based test system according to claim 7 wherein the light emitting fluorophore is allophycocyanin or streptavidin-allophycocyanin, and the ultra-violet excitable fluorophore is europium.

9. A homogeneous time resolved fluorescence-based test system according to claim 7 wherein the light emitting fluorophore is selected from the group of sulfonated rhodamine having an optimal excitation wavelength at 546 nm, rhodamine, or Cy3 and wherein the ultra-violet excitable fluorophore is terbium.

10. A method for identifying a compound that interferes with the formation of the RSV six-helix bundle of F1 comprising:

providing a first helical polypeptide consisting of the sequence of IQN57 (SEQ ID NO: 1);

providing a second helical polypeptide consisting of the sequence of C45 (SEQ ID NO: 2) wherein said IQN57 is labeled with a light emitting fluorophore and said C45 is labeled with an ultra-violet excitable fluorophore;

providing a test composition comprising the compound;

measuring the degree of complex formation between the first helical polypeptide and the second helical polypeptide in the presence of the test composition comprising the compound using fluorescence resonance energy transfer; and comparing the measured degree of complex formation to the degree of complex formation between the first helical polypeptide and the second helical polypeptide in the absence of the test composition comprising the compound to identify the compound that interferes with the formation of the RSV six-helix bundle of F1.

11. A method for identifying a compound that interferes with the formation of the RSV six-helix bundle of F1 according to claim 10 wherein said IQN57 sequence comprises a linker between the label and the IQ-moiety of the IQN57 sequence.

12. A method for identifying a compound that interferes with the formation of the RSV six-helix bundle of F1 according to claim 11 wherein the linker is attached to the N-terminal IQ-end of the IQN57 sequence.

13. A method for identifying a compound that interferes with the formation of the RSV six-helix bundle of F1 according to claim 11 wherein said linker is selected from the group of an antibody-antibody complex, antibody-antigen complex or streptavidin-biotin system.

14. A method for identifying a compound that interferes with the formation of the RSV six-helix bundle of F1 according to claim 10 wherein the ultra-violet excitable fluorophore is selected from the group of lanthanides and wherein the light emitting fluorophore matches the excitation wavelength of the selected lanthanide.

15. A method for identifying a compound that interferes with the formation of the RSV six-helix bundle of F1 according to claim 14 wherein the light emitting fluorophore is allophycocyanin or streptavidin-allophycocyanin, and the ultra-violet excitable fluorophore is europium.

16. A method for identifying a compound that interferes with the formation of the RSV six-helix bundle of F1 according to claim 14 wherein the light emitting fluorophore is selected from the group of sulfonated rhodamine having an optimal excitation wavelength at 546 nm, rhodamine, or Cy3 and wherein the ultra-violet excitable fluorophore is terbium.

17. A method for identifying the mechanism of inhibition of the formation of the RSV six-helix bundle of F1 comprising:

providing a first helical polypeptide consisting of the sequence of IQN57 (SEQ ID NO: 1);

providing a second helical polypeptide consisting of the sequence of C45 (SEQ ID NO: 2) wherein said IQN57 is labeled with a light emitting fluorophore and said C45 is labeled with an ultra-violet excitable fluorophore;

providing a test composition comprising a compound that interferes with the formation of the six-helix bundle of F1;

measuring the degree of complex formation between the first helical polypeptide and the second helical polypeptide in the presence of the test composition comprising a compound that interferes with the formation of the six-helix bundle of F1 using fluorescence resonance energy transfer; and comparing the measured degree of complex formation to the degree of complex formation between the first helical polypeptide and the second helical polypeptide in the absence of the test composition comprising the compound that interferes with the formation of the six-helix bundle of F1 to identify the mechanism of inhibition of the formation of the RSV six-helix bundle of F1.

* * * * *